(12) United States Patent
Thoma et al.

(10) Patent No.: US 12,269,636 B2
(45) Date of Patent: Apr. 8, 2025

(54) DEVICE AND METHOD FOR GENERATING A LIQUID FILM OF A LIQUID MEDIUM IN A FILM BAG, AND ASSEMBLY FOR THE CONTROLLED EXPOSURE OF A LIQUID MEDIUM IN A FILM BAG USING PHYSICAL RADIATION

(71) Applicant: FRAUNHOFER-GESELLSCHAFT ZUR FÖRDERUNG DER ANGEWANDTEN FORSCHUNG E.V., Munich (DE)

(72) Inventors: Martin Thoma, Stuttgart (DE); Bastian Standfest, Stuttgart (DE); Michael Klinger, Stuttgart (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 41 days.

(21) Appl. No.: 17/920,072

(22) PCT Filed: Apr. 19, 2021

(86) PCT No.: PCT/EP2021/060075
§ 371 (c)(1),
(2) Date: Oct. 20, 2022

(87) PCT Pub. No.: WO2021/213973
PCT Pub. Date: Oct. 28, 2021

(65) Prior Publication Data
US 2023/0174260 A1 Jun. 8, 2023

(30) Foreign Application Priority Data
Apr. 21, 2020 (DE) ...................... 10 2020 205 036.8

(51) Int. Cl.
*B65B 55/16* (2006.01)
*A61L 2/08* (2006.01)
(Continued)

(52) U.S. Cl.
CPC ................ *B65B 55/16* (2013.01); *A61L 2/08* (2013.01); *A61L 2/26* (2013.01); *B65B 55/04* (2013.01);
(Continued)

(58) Field of Classification Search
CPC ........ B01F 31/55; B01F 33/05; B01F 33/055; A61L 2/08; A61L 2/0029; B65B 55/02;
(Continued)

(56) References Cited

U.S. PATENT DOCUMENTS 2,001,555 A * 5/1935 Trebler .................. A23C 3/076
422/186.3
3,081,485 A * 3/1963 Steigerwald .......... D02J 13/003
264/290.5
(Continued)

FOREIGN PATENT DOCUMENTS

CN 1292027 A 4/2001
CN 101115405 A 1/2008
(Continued)

OTHER PUBLICATIONS

International Search Report (English and Deutsch) and Written Opinion of the International Searching Authority (Deutsch) issued in PCT/EP2021/060075, mailed Jul. 29, 2021; ISA/EP.
(Continued)

*Primary Examiner* — Gloria R Weeks
*Assistant Examiner* — Mobeen Ahmed
(74) *Attorney, Agent, or Firm* — Harness, Dickey & Pierce, P.L.C.; Stephen T. Olson

(57) ABSTRACT

A device for generating a liquid film of a liquid medium in a film bag comprising two accumulating surfaces, a braking
(Continued)

Figure 1:
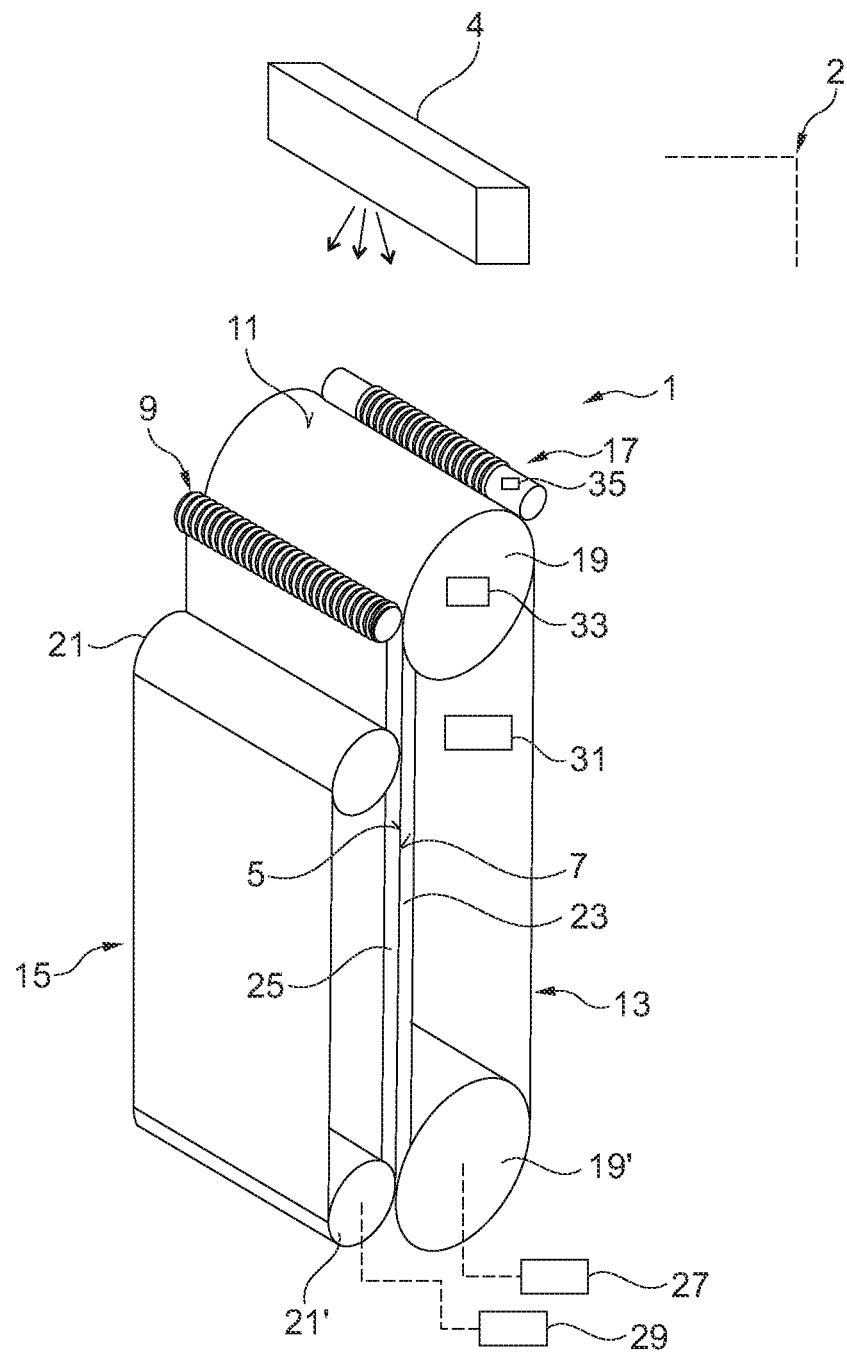

element, and a running surface are described herein. The device may further comprise a tensioning element. Also provided is an assembly for the controlled exposure of a liquid medium in a film bag using physical radiation and a method for generating a liquid film of a liquid medium in a film bag.

11 Claims, 6 Drawing Sheets

(51) Int. Cl.
    *A61L 2/26*     (2006.01)
    *B65B 55/04*     (2006.01)
    *B65B 57/02*     (2006.01)
    *B65B 55/10*     (2006.01)

(52) U.S. Cl.
    CPC ........... *B65B 57/02* (2013.01); *A61L 2202/11* (2013.01); *A61L 2202/23* (2013.01); *B65B 55/103* (2013.01); *B65B 55/106* (2013.01)

(58) Field of Classification Search
    CPC ... B65B 2210/06; B65B 55/04; B65B 55/103; B65B 55/106; B65B 55/12; B65B 55/16
    See application file for complete search history.

(56) References Cited

U.S. PATENT DOCUMENTS

| | | | | |
|---|---|---|---|---|
| 4,048,504 A * | 9/1977 | Bosshard | B01J 19/085 | 250/434 |
| 4,449,050 A * | 5/1984 | Kamhi | G07D 11/10 | 134/122 R |
| 4,708,715 A * | 11/1987 | Troutner | A61M 1/3683 | 439/235 |
| 4,866,282 A * | 9/1989 | Miripol | A61M 1/3681 | 250/455.11 |
| 4,952,812 A * | 8/1990 | Miripol | A61L 2/0011 | 250/455.11 |
| 5,133,932 A * | 7/1992 | Gunn | A61L 2/0011 | 210/243 |
| 5,290,221 A * | 3/1994 | Wolf, Jr. | A61M 1/3683 | 604/20 |
| 5,459,322 A * | 10/1995 | Warkentin | A61M 1/3681 | 250/455.11 |
| 5,527,704 A * | 6/1996 | Wolf, Jr. | C12M 37/00 | 422/186.3 |
| 5,557,098 A * | 9/1996 | D'Silva | G06K 7/14 | 250/559.4 |
| 5,762,867 A * | 6/1998 | D'Silva | A61M 1/3683 | 422/23 |
| 5,786,598 A * | 7/1998 | Clark | B65B 55/02 | 250/455.11 |
| 5,868,695 A * | 2/1999 | Wolf, Jr. | A61L 2/08 | 604/20 |
| 5,922,278 A * | 7/1999 | Chapman | A61L 2/0011 | 250/455.11 |
| 5,925,885 A * | 7/1999 | Clark | A61L 2/081 | 250/455.11 |
| 5,997,812 A * | 12/1999 | Burnham | C02F 1/48 | 210/695 |
| 6,190,609 B1 * | 2/2001 | Chapman | A61M 1/3683 | 435/283.1 |
| 6,212,255 B1 * | 4/2001 | Kirk | G21K 5/08 | 378/65 |
| 6,245,570 B1 * | 6/2001 | Grimm | A61L 2/10 | 436/55 |
| 6,369,394 B1 * | 4/2002 | Lee | B01F 31/55 | 250/455.11 |
| 6,433,344 B1 * | 8/2002 | Salisbury | B65B 55/08 | 250/455.11 |
| 6,566,659 B1 * | 5/2003 | Clark | A23L 3/28 | 422/23 |
| 6,596,230 B1 * | 7/2003 | Woo | A61M 1/3681 | 250/433 |
| 6,753,536 B2 * | 6/2004 | Humphreys | A61L 2/04 | 250/455.11 |
| 6,756,597 B2 * | 6/2004 | Avnery | G21K 5/10 | 210/402 |
| 6,843,961 B2 * | 1/2005 | Hlavinka | C07F 13/005 | 422/1 |
| 7,038,219 B2 * | 5/2006 | Clark | A61L 12/06 | 250/455.11 |
| 7,077,559 B2 * | 7/2006 | Hlavinka | A61L 2/10 | 422/44 |
| 8,048,055 B2 * | 11/2011 | Hlavinka | A61M 1/3683 | 604/408 |
| 8,197,117 B2 * | 6/2012 | White | B01F 31/55 | 366/218 |
| 9,441,193 B2 * | 9/2016 | Tanaka | C12M 23/14 | |
| 9,511,164 B2 * | 12/2016 | Dayton | A61L 2/24 | |
| 2008/0286424 A1 * | 11/2008 | Patel | A23C 3/07 | 426/240 |
| 2010/0139222 A1 * | 6/2010 | Federle | B65B 57/14 | 53/474 |
| 2010/0162664 A1 * | 7/2010 | Setozaki | B65B 43/12 | 53/558 |
| 2011/0294157 A1 * | 12/2011 | Bontinck | A61L 2/081 | 250/428 |
| 2014/0357462 A1 * | 12/2014 | Voss | B65B 9/13 | 53/64 |
| 2016/0096274 A1 * | 4/2016 | Baylor | B25J 9/1687 | 700/259 |
| 2020/0017245 A1 * | 1/2020 | Tsuruta | B65B 61/005 | |

FOREIGN PATENT DOCUMENTS

| | | |
|---|---|---|
| CN | 105197312 A | 12/2015 |
| CN | 206050139 U | 3/2017 |
| DE | 4209509 C1 | 6/1993 |
| DE | 4225183 A1 | 2/1994 |
| DE | 102015224206 B3 * | 12/2016 |
| WO | WO-2018051784 A1 * | 3/2018 |

OTHER PUBLICATIONS

International Preliminary Report on Patentability issued in PCT/EP2021/060075, mailed Nov. 3, 2022.
Chinese Office Action regarding Patent Application No. 2021800303835. dated Jan. 10, 2024.
Second Chinese Office Action regarding Application No. 202180030383.5, dated May 16, 2024.

* cited by examiner

DEVICE AND METHOD FOR GENERATING A LIQUID FILM OF A LIQUID MEDIUM IN A FILM BAG, AND ASSEMBLY FOR THE CONTROLLED EXPOSURE OF A LIQUID MEDIUM IN A FILM BAG USING PHYSICAL RADIATION

CROSS REFERENCE TO RELATED APPLICATIONS

This application is a U.S. National Phase Application under 35 U.S.C. 371 of International Application No. PCT/EP2021/060075, filed on Apr. 19, 2021, which claims priority to German Patent Application No. 10 2020 205 036.8, filed on Apr. 21, 2020. The entire disclosures of the above applications are expressly incorporated by reference herein.

The invention relates to a device for generating a liquid film of a liquid medium in a film bag, an assembly for the controlled exposure of a liquid medium in a film bag using physical radiation using such a device, and a method for generating a liquid film of a liquid medium in a film bag.

Modern methods for providing and processing liquid media, in particular liquid biological media, often provide for controlled exposure of such a liquid medium to physical radiation, for example for sterilization or disinfection, for preservation, for inactivation of cell proliferation, or to inactivate contained viruses. In order to be able to precisely control the radiation dose acting on the liquid medium, it is particularly important that an irradiated liquid film with a homogeneous and temporally constant layer thickness is produced. For example, in electron irradiation, the accelerated electrons lose energy with increasing penetration depth, so that the depth dose decreases. The layer thickness on the one hand and also the fluid velocity of the liquid medium in the area of the irradiated liquid film on the other hand each have a direct influence on the applied dose. If liquid media are to be irradiated automatically, a uniform, controllable liquid film is therefore required to ensure homogeneous treatment.

German patent DE 10 2015 224 206 B3 discloses a device for generating such a liquid film, wherein a film bag is clamped between two guide plates and tensioned and transported by means of a friction wheel. During transportation of the film bag, a friction surface between the film bag and the guide plates decreases, wherein the bag tension also decreases. This leads to an inhomogeneity of the layer thickness in the film bag. In addition, the device does not enable layer thickness-dependent control of the bag tension or the transport speed. In particular, bag tension on the one hand and transport of the film bag on the other hand are coupled with each other and cannot be adjusted independently of each other. This can be improved, particularly with regard to reproducible irradiation results and the controlled introduction of a specific radiation dose.

The invention is therefore based on the problem of providing a device for generating a liquid film of a liquid medium in a film bag, an assembly for the controlled exposure of the liquid medium in the film bag to physical radiation, and a method for generating a liquid film of a liquid medium in a film bag, wherein said disadvantages are at least reduced, preferably eliminated.

The problem is solved by providing the present technical teaching, in particular the teaching of the independent claims as well as the embodiments disclosed in the dependent claims and the description.

The problem is solved in particular by providing a device for generating a liquid film of a liquid medium in a film bag, which has two accumulating surfaces spaced apart by an accumulating distance, between which the film bag can be arranged and transported along a transport direction. A braking element is arranged downstream of the accumulating surfaces in the transport direction, which braking element is arranged to brake the film bag. The device further comprises a running surface convexly curved in the transport direction, which is arranged and arranged in such a way that the film bag braked by the braking element can be clamped on the running surface behind the braking element. At least a first accumulating surface of the two accumulating surfaces is formed at least in regions by a driven first conveyor belt, which is arranged to convey the film bag in the transport direction. The device has a controllable tensioning element downstream of the braking element in the transport direction, which is arranged to span the film bag on the running surface between the braking element and the tensioning element. The first conveyor belt or a belt drive for the first conveyor belt is controllable independently of the controllable tensioning element. In particular, because the device proposed here has on the one hand the driven first conveyor belt for transporting the film bag through the device and on the other hand the controllable tensioning element for spanning the film bag, it is possible to set, in particular regulate, the bag tension of the film bag on the one hand and the transport speed through the device on the other hand independently of one another. This ensures a homogeneous and temporally constant layer thickness and thus, not least, the introduction of a controlled dose into the liquid medium when the film bag is exposed to physical radiation.

The controllable tensioning element is thereby controllable in particular in order to influence, in particular to adjust, preferably to regulate the bag tension of the film bag. The driven first conveyor belt is preferably controllable, or the belt drive for the first driven conveyor belt is preferably controllable, in order to adjust, preferably regulate, the transport speed of the film bag through the device.

The first conveyor belt or the belt drive for the first conveyor belt can be controlled independently of the controllable tensioning element, so that the setting, preferably adjustment, of the bag tension is decoupled from the setting, preferably adjustment, of the transport speed for the film bag.

Last but not least, with the device proposed here, it can be advantageously avoided that a decreasing friction surface between the film bag and the accumulating surfaces during transport leads to the bag tension decreasing. Thus, a temporally increasing inhomogeneity of the layer thickness in the film bag can also be advantageously avoided.

Insofar as the terms "in front of" and "behind" are used here, these are to be understood in particular with reference to the transport direction. Thus, an element arranged behind another element is arranged behind the other element in the transport direction, so that it is reached after the other element when the film bag is transported by the device. Accordingly, an element arranged in front of another element is arranged in front of this other element in the transport direction, so that it is reached first, before the other element, when a film bag is transported through the device.

A film bag is understood here to be a bag formed from at least one film, in particular plastic film, which is set up for receiving, storing, transporting, and processing a liquid medium, in particular a liquid biological medium. Known film bags of this type are, for example, blood bags or infusion bags. However, such film bags are also used, for example, to hold virus suspensions in the production of vaccines. A variety of other applications as well as other liquid media in connection with such film bags are possible. In particular, the film bag has a base film and a cover film, wherein a closed compartment is formed between the base film and the cover film in which the liquid medium is accommodated. In operation of the device proposed here, the base film in particular lies directly on the running surface, while the cover film is stretched over the base film and the liquid medium.

The film bag can be configured in particular as a so-called sealed edge bag. In this case, the base film and the cover film are provided separately from one another and are welded or bonded to one another via weld seams, i.e. sealed edges, in such a way that the closed compartment is formed between the base film and the cover film. Alternatively, the film bag is configured as a so-called tubular bag, wherein a film tube is welded or bonded in sections or at ends with a flat seam, wherein the closed compartment is formed between two seams. The flat seams give the tubular bag as a whole a flattened shape, and it is also possible to distinguish an upper film section as a cover film and a lower film section as a base film, as in the case of the sealed-edge bag. The film bag is preferably formed from at least one flexible and within limits elastic plastic film, particularly preferably PE or PET/PE composite material, PP, or also PVC.

In the device proposed here, chains of separate compartments lying one behind the other can also be used as a film bag chain. In particular, the device proposed here can also be part of an automatic line or transport line along which a plurality of film bags, in particular a film bag chain, is conveyed.

In particular, the accumulating surfaces are spaced apart from one another along the transport direction by the accumulating distance. They are thus arranged in particular to the side of the transport direction, on both sides of a film bag to be transported.

The accumulating surfaces are preferably flat, at least in some areas.

In particular, the braking element is set up to brake the cover film of the film bag.

In particular, the tensioning element is set up to tension the cover film of the film bag.

The tensioning element is preferably controllable as a function of a predetermined, preferably parameterizable layer thickness of the liquid film in the film bag.

Preferably, the device comprises as the belt drive for the first conveyor belt a first belt drive which is drive-actively connected to the first conveyor belt and is arranged to drive the first conveyor belt. Alternatively, it is possible that the first conveyor belt is arranged to cooperate with a drive means or belt drive provided separately from the device in order to be driven by this drive means or belt drive.

The device preferably has a control device that is set up to control the tensioning element. In a preferred embodiment, the control device is also set up to control the first belt drive or the separate belt drive for the first conveyor belt.

Preferably, the first transport surface is completely formed by the first conveyor belt.

The running surface is preferably formed in some areas by the first conveyor belt. This represents a particularly simple and integrated embodiment of the device, especially since the film bag can be transported by means of the first conveyor belt both in the area of the accumulating surfaces and in the area of the running surface.

In particular, the running surface is preferably configured on a cylinder roller over which the first conveyor belt runs during operation of the device. Preferably, the first conveyor belt is tensioned between two first cylinder rollers and runs on the two first cylinder rollers as an endless belt during operation of the device. The running surface is arranged on a first first cylinder roller of the two first cylinder rollers.

The first conveyor belt is preferably formed from steel, in particular as a steel belt, or consists of steel. Alternatively, it is possible that the first conveyor belt is formed from a plastic, in particular fluororubber (FKM), or consists of a plastic, in particular fluororubber (FKM).

Preferably, the accumulating surfaces are oriented at least substantially vertically, preferably vertically. Preferably, the first conveyor belt runs vertically upwards in the region of the first accumulating surface during operation of the device, the film bag is thus also transported upwards in the region of the accumulating surfaces during operation of the device. Preferably, the running surface is arranged at an upper end of the device.

Without wishing to be bound by theory, the operation of the device is based at least approximately on the following considerations: If the film bag is spanned over the convex running surface, the cover film is arranged along a greater circumferential distance than the base film resting directly on the running surface due to the greater distance to the center of curvature of the convex running surface. The flexible cover film, which can be stretched within limits, is thus stretched taut in the area of the running surface, and a controlled constriction is created locally in the film bag, which enables the desired formation of the uniform liquid film there. The formation of the liquid film during transport of the film bag over the running surface takes place in that, in a first phase, the liquid medium is retained in the partial compartment of the film bag still arranged in front of the braking element due to the constriction formed by the braking effect of the braking element and the stretching of the film bag over the convex running point, wherein it is therefore initially not transported further, or only to a lesser extent, compared to the film bag itself. However, since inflation of the partial compartment arranged between the accumulating surfaces is prevented by the volume restriction in the accumulating space formed by the accumulating distance, a local pressure increase occurs there, and in a second phase the accumulated liquid medium within the compartment is actively pumped in the transport direction of the film bag, wherein, due to the embodiment of the device proposed here, it flows through in a controlled and uniform manner between the films spanned on the convex running surface, i.e. the base film and the cover film, thereby overtaking the film bag and being received in the partial compartment of the film bag arranged behind the tensioning element, which can expand freely. Thus, at the convex running surface between the braking element and the tensioning element, there is a partial compartment of the film bag in which the contained liquid medium is present as a thin liquid film, with a surface/volume ratio favorable for dose-controlled exposure to physical radiation.

The liquid film can preferably be produced there with a homogeneous thickness of 200 µm or less.

Preferably, the film thickness is from at least 20 µm to at most 200 µm.

In particular, the device proposed here enables the layer thickness to be controlled independently of the transport speed by decoupling the transport and the generation of the bag tension of the film bag.

According to a further development of the invention, it is provided that a second accumulating surface of the two accumulating surfaces is formed at least in some areas by a second conveyor belt. Advantageously, both accumulating surfaces can thus be formed at least in some areas by conveyor belts, so that a particularly well-defined transport of the film bag through the conveyor belts and in particular between the conveyor belts is possible.

Preferably, the second transport surface is completely formed by the second conveyor belt.

The second conveyor belt is preferably formed of steel, preferably the second conveyor belt consists of steel. In particular, it is preferably configured as a steel belt. Alternatively, it is possible that the second conveyor belt is formed from a plastic, in particular fluororubber (FKM), or consists of a plastic, in particular fluororubber (FKM).

According to a further development of the invention, it is provided that the first conveyor belt is arranged on a first accumulating plate so as to be displaceable relative to the first accumulating plate. This advantageously provides an at least partially guided and supported displacement for the first conveyor belt. In addition, the first accumulating plate advantageously absorbs a contact pressure of the film bag and supports it.

Preferably, the second conveyor belt is arranged on a second accumulating plate so as to be displaceable relative to the second accumulating plate. In this way, the second conveyor belt is advantageously guided and supported at least in certain areas, wherein the contact pressure of the film bag can also be absorbed and supported by the second accumulating plate.

Particularly preferably, the first conveyor belt is arranged on the first accumulating plate so as to be displaceable relative thereto, wherein the second conveyor belt being arranged on the second accumulating plate so as to be displaceable relative thereto. This enables particularly stable guidance and support of the film bag and of the conveyor belts during transport of the film bag. In particular, the film bag can be arranged between the accumulating plates and transported there by the conveyor belts.

According to a further development of the invention, it is provided that the first conveyor belt and the second conveyor belt are mechanically coupled to each other with respect to their running speed. This represents a particularly simple embodiment of the device, in which in particular the second conveyor belt can be driven by the same belt drive as the first conveyor belt. At the same time, undesirable differences in running speed between the conveyor belts are advantageously avoided.

Alternatively, it is preferably provided that the first conveyor belt and the second conveyor belt are each assigned an independently controllable belt drive. This means in particular that the first belt drive for the first conveyor belt can be controlled independently of a second belt drive for the second conveyor belt—and vice versa. This enables a particularly flexible control of the belt drives and a particularly flexible selection of the different running speeds, in particular in order to additionally influence transport parameters for the film bag. Preferably, the running speeds for the first conveyor belt and the second conveyor belt are adjustable—preferably electronically. In particular, the control device is preferably operatively connected to the first belt drive and to the second belt drive and is set up to preset the running speeds—in particular independently of one another. Advantageously, this makes it possible to move the two conveyor belts at different speeds or even—at least temporarily—in different directions in order to influence transport parameters for the film bag as required and in a particularly flexible manner.

It is possible that the accumulating distance is constant along the transport direction, or that the accumulating distance alternatively tapers continuously in the transport direction. In particular, it is possible that the first accumulating surface and the second accumulating surface are configured plane, preferably plane-parallel to each other. The accumulating distance can, for example, be approximately 1 mm, preferably it is at most 1 mm or is smaller than 1 mm.

In a preferred embodiment, it is also possible for the accumulating distance to exhibit a discrete change along the transport direction, in particular a discrete tapering in the transport direction. Preferably, at least one of the accumulating surfaces, selected from the first accumulating surface and the second accumulating surface, has a step, wherein the accumulating distance changing, in particular tapering, in the region of the step, in particular from a first constant distance value in front of the step—for example 1 mm—to a second, smaller constant distance value behind the step—for example 0.5 mm. The second distance value is preferably about half of the first distance value, preferably half of the first distance value. The modification, taper or step is preferably arranged in an area in front of the braking element, in particular—measured in the transport direction—at a distance from the braking element which is smaller than half the length, measured in the transport direction, of one of the accumulating surfaces, in particular of the accumulating surface having the step, preferably smaller than one third of the length, in particular smaller than one quarter of the length.

According to a further development of the invention, it is provided that at least one of the accumulating surfaces is displaceable relative to the other accumulating surface of the two accumulating surfaces in such a way that the accumulating distance is adjustable. This advantageously enables an adjustment of the accumulating distance, in particular as a further transport parameter with a view to the transport of the film bag. In particular, a frictional force between the film bag and the accumulating surfaces can be varied in this way—preferably also dynamically during the transport of the film bag through the device.

According to a preferred embodiment, the accumulating distance is constantly adjustable along the transport direction. In this case, the accumulating surfaces are arranged at least substantially parallel to each other, preferably parallel to each other.

Alternatively or additionally, it is preferably provided that the accumulating distance can be set to taper along the transport direction. The accumulating surfaces are then oriented at least slightly obliquely to one another, virtually in the form of a wedge, wherein the accumulating distance between the accumulating surfaces, as seen along the transport direction, becomes smaller. Thus, in particular, the friction between the film bag and the accumulating surfaces becomes greater towards the braking element. By adjusting the taper of the accumulating distance, a further transport parameter can be advantageously varied.

According to a further development of the invention, it is provided that the braking element is configured as a brake roller. Preferably, the brake roller has at least one element that increases static friction, particularly preferably a plurality of friction rings that are mounted on a roller base body of the brake roller and are spaced apart from one another in the axial direction of the brake roller. In a preferred embodiment, the friction rings are in the form of O-rings.

Preferably, the brake roller is speed-coupled to the first conveyor belt. This represents a particularly simple embodiment of the brake roller as a passively braked braking element, wherein neither separate braking devices nor a separate drive for the brake roller are required. In particular, the brake roller is preferably speed-coupled to the first conveyor belt in that it bears against the first conveyor belt with the at least one element that increases static friction and is thereby frictionally coupled to the first conveyor belt. In particular, it is thus moved synchronously by the first conveyor belt and preferably cannot be accelerated relative to the first conveyor belt at least by the forces or torques occurring in normal operation of the device.

Alternatively, it is preferred that the brake roller is driven independently of the first conveyor belt. This allows particularly flexible adjustment of the transport parameters and additional influence on the bag tension. In this embodiment, the brake roller can rotate in particular at a speed independent of the running speed of the first conveyor belt.

Alternatively, it is preferably possible for the brake roller to be actively or passively braked. Active braking can be provided, for example, by a controllable braking mechanism, such as brake shoes, or by an electric machine that is operatively connected to the brake roller and controlled in the braking direction, for example operated as a generator. Passive braking can be provided, for example, by a suitably adjusted centrifugal brake.

According to a further development of the invention, it is provided that the tensioning element is configured as a tensioning roller. This also represents a simple as well as reliable and functional embodiment of the device. The control device, which is operatively connected to the tensioning element, is in particular set up to control the tensioning element in a torque-controlled manner, preferably in a torque-regulated manner, or in a speed-controlled manner, preferably in a speed-regulated manner, as a function of the determined, preferably parameterizable layer thickness of the liquid film to be produced. In particular, when the tensioning element is actuated in a torque-controlled or torque-regulated manner, this is preferably done in such a way that no slip occurs between the tensioning element, in particular the tensioning roller, and the cover film of the film bag. The cover film is thus advantageously subjected—in particular by means of static friction—to a constant temporal force resulting from the torque of the tensioning roller, from which the bag tension results.

In contrast, a speed-controlled, preferably speed-regulated, control of the tensioning element is a simpler embodiment which nevertheless enables good definition of the bag tension. However, slippage between the cover film and the tensioning roller may be accepted. The tensioning force introduced into the cover film can also result in particular from sliding friction between the tensioning roller and the cover film.

According to a further development of the invention, it is provided that the device comprises a temperature control device which is arranged to temper the running surface. In this way, the temperature of the liquid film can be advantageously adjusted, in particular in a range favorable for exposure to physical radiation or the desired effect.

The temperature control device is preferably set up to heat the running surface.

Alternatively or additionally, the device preferably has a cooling device that is set up to cool the tensioning element. With the tensioning element, the film bag and thus the liquid medium arranged in the film bag can preferably be cooled at the same time, in particular after possible heating in the area of the running surface. This advantageously enables any temperature increase provided for treatment of the liquid medium to be effected only for a comparatively short time, so that in particular the durability of the liquid medium is not jeopardized.

According to a further development of the invention, it is provided that the device has a measuring device for determining a layer thickness of the liquid film. In this way, the layer thickness can be advantageously detected and, in particular, adjusted—preferably by controlling the controllable tensioning element and/or at least the first conveyor belt.

"Determination of the layer thickness" does not necessarily mean that the layer thickness is explicitly determined. Rather, for the purpose of reproducible operation of the device while maintaining a temporally constant layer thickness and, in particular, a controlled exposure of the liquid medium to physical radiation, it is sufficient if a physical variable is indirectly detected that can serve as a measure of the layer thickness or is at least unambiguously related to the layer thickness, this physical variable being adjusted in such a way that the layer thickness is temporally constant. Of course, it is also possible that the coating thickness is explicitly detected and preferably adjusted.

The measuring device is preferably set up to determine the layer thickness by means of pressure measurement, optically, electrically or electronically, and/or by detecting a flow velocity of the liquid medium in the film bag.

For a determination by means of pressure measurement, a pressure sensor is preferably provided, which is arranged in front of the braking element in the transport direction. The pressure sensor preferably detects a pressure as a measure of flow resistance for the liquid medium, which is dependent on the layer thickness on the running surface. The pressure is preferably detected continuously or at discrete time intervals. In particular, a relative change over time of the pressure sensed by the pressure sensor is preferably evaluated. A model can then preferably be used to calculate back to the coating thickness, and/or the pressure can be adjusted to a constant value in a predefined pressure range in order to keep the coating thickness constant.

An optical determination of the film thickness is preferably selected from a group consisting of: An imaging method, the detection of a shading, the detection of an intensity, in particular a color or brightness of the liquid film on the running surface, and an interference measurement.

An imaging method as well as a detection of a shading, in particular the detection of the shading of a light source by the liquid film, each allows a direct measurement of the layer height.

The measurement of an intensity, in particular a color intensity and/or a brightness of the liquid film also enables the layer thickness to be determined, in particular if the liquid medium is luminescent, fluorescent or otherwise colored.

Finally, an interference measurement also enables direct determination of the layer thickness, in particular by the device having a gap-forming element which is arranged opposite the running surface in such a way that an optical gap is bounded on the one hand by the cover film at the highest point of the convex running surface and thus at the same time at the maximum of the liquid film, and on the other hand by the gap-forming element. Thus, an interference pattern arising in transmission through the gap formed in this way depends directly on the film thickness.

An electrical or electronic measurement includes, in particular, a capacitive measurement and/or a measurement by means of high-frequency detuning of the layer thickness.

Since the liquid film is formed in particular dynamically by the liquid medium flowing in the film bag and overtaking the film bag in particular in the region of the running surface, the film thickness is directly related to the flow velocity of the liquid medium in the film bag. Thus, the layer thickness can also be determined by detecting the flow velocity of the liquid medium in the film bag in the region of the running surface. This can be detected, for example, using a PIV (Particle Image Velocimetry) method, an ultrasonic method, or another non-contact flow velocity measurement method. Preferably, the flow velocity is measured on the inlet and outlet side.

Finally, the problem is also solved by providing an assembly for the controlled exposure of a liquid medium in a film bag to physical radiation, the assembly comprising a device according to the invention or a device according to one of the previously described embodiments. The assembly further comprises a radiation source of physical radiation arranged and adapted to irradiate the film bag in the region of the convex running surface. In connection with the assembly, the advantages already explained in connection with the device arise in particular. In particular, the irradiation takes place where the liquid film is produced with—by the device proposed here—a well-defined and temporally constant layer thickness, especially in the maximum of the convex running surface. Thus, the exposure of the liquid medium to the physical radiation can be performed in a dose-controlled manner, in particular.

Physical radiation is generally understood to be a physical radiation phenomenon, whether particle radiation or wave radiation. Preferably, the radiation source is arranged to emit ionizing radiation. Preferably, the radiation source is arranged to emit electromagnetic radiation or particle radiation, in particular beta radiation, hard or soft X-ray radiation, ultraviolet radiation, visible electromagnetic radiation (light), infrared or thermal radiation, terahertz radiation, microwave radiation, atomic ion radiation, proton radiation, positron radiation, or any other type of radiation.

Finally, the problem is also solved by creating a method for generating a liquid film of a liquid medium in a film bag, wherein a film bag is transported in the transport direction by a device according to the invention or a device according to one of the embodiments described above, and wherein a uniform liquid film, preferably having a temporally constant layer thickness, is produced by controlling at least one belt drive for the first conveyor belt, on the one hand, and the tensioning element, on the other hand, independently of one another. In connection with the method, the advantages already described in connection with the device and the assembly arise in particular.

The fact that the belt drive on the one hand and the tensioning element on the other are controlled independently of each other means in particular that there is no direct dependence between the control of the belt drive for the first conveyor belt and the control of the tensioning element. An indirect or mediate dependence is not excluded, in particular not in such a way that the control of the layer thickness as a superordinate variable can require an adaptation of both the control of the belt drive and the control of the tensioning element and possibly even a coordination of the control of the belt drive and the control of the tensioning element. In particular, however, there is no direct mechanical, electronic or other logical coupling between the belt drive and the control of the tensioning element in the sense that a change in the control of one element directly results in a change in the control of the other element.

Figure 2:
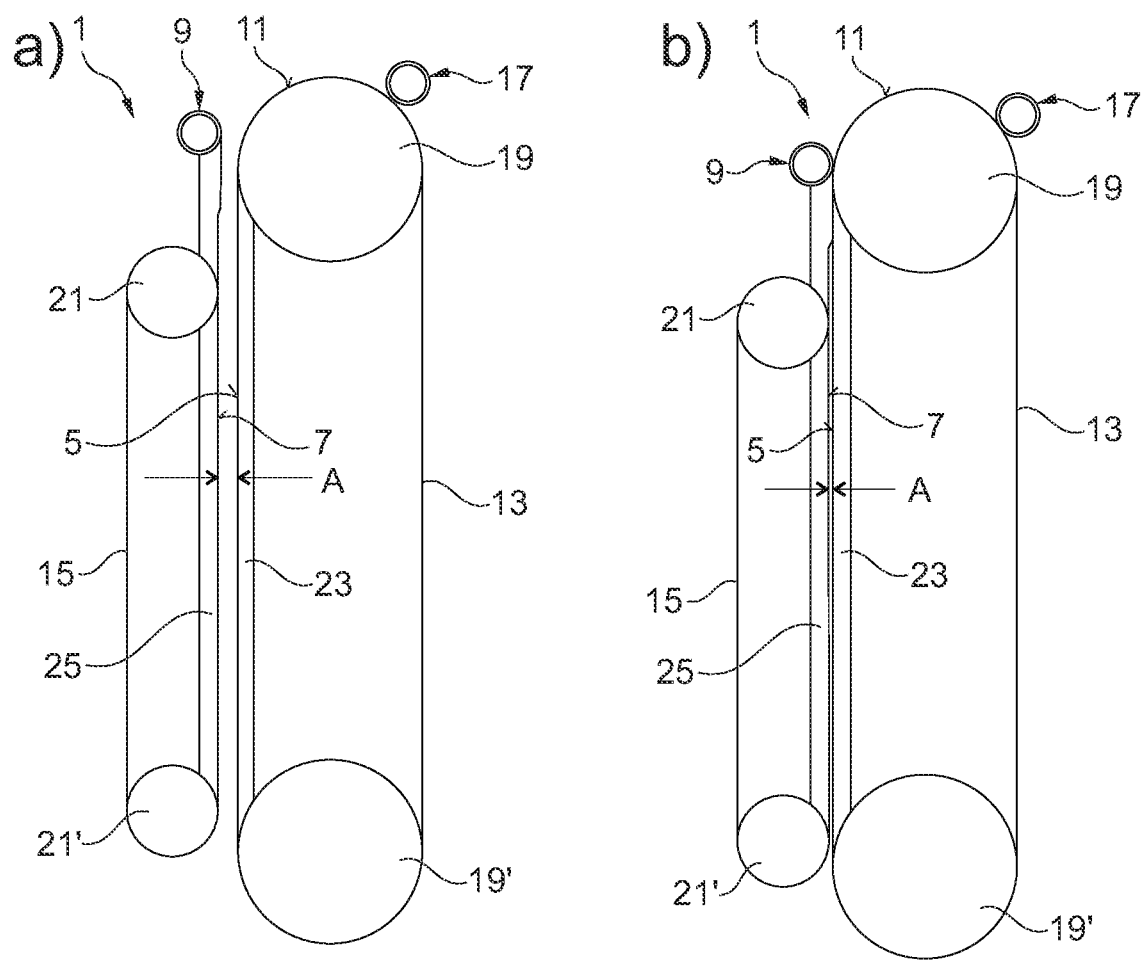
Figure 3:
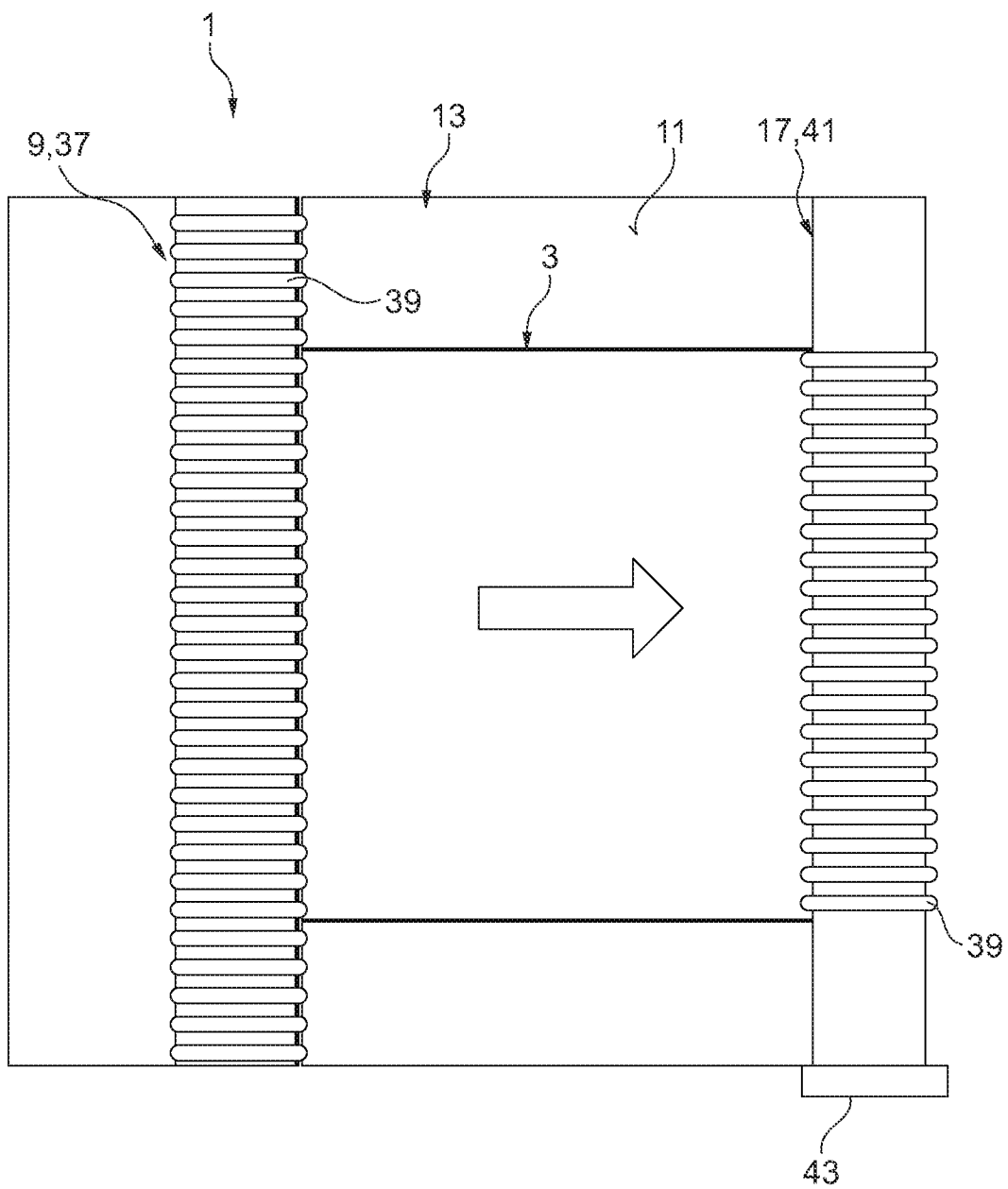
Figure 4:
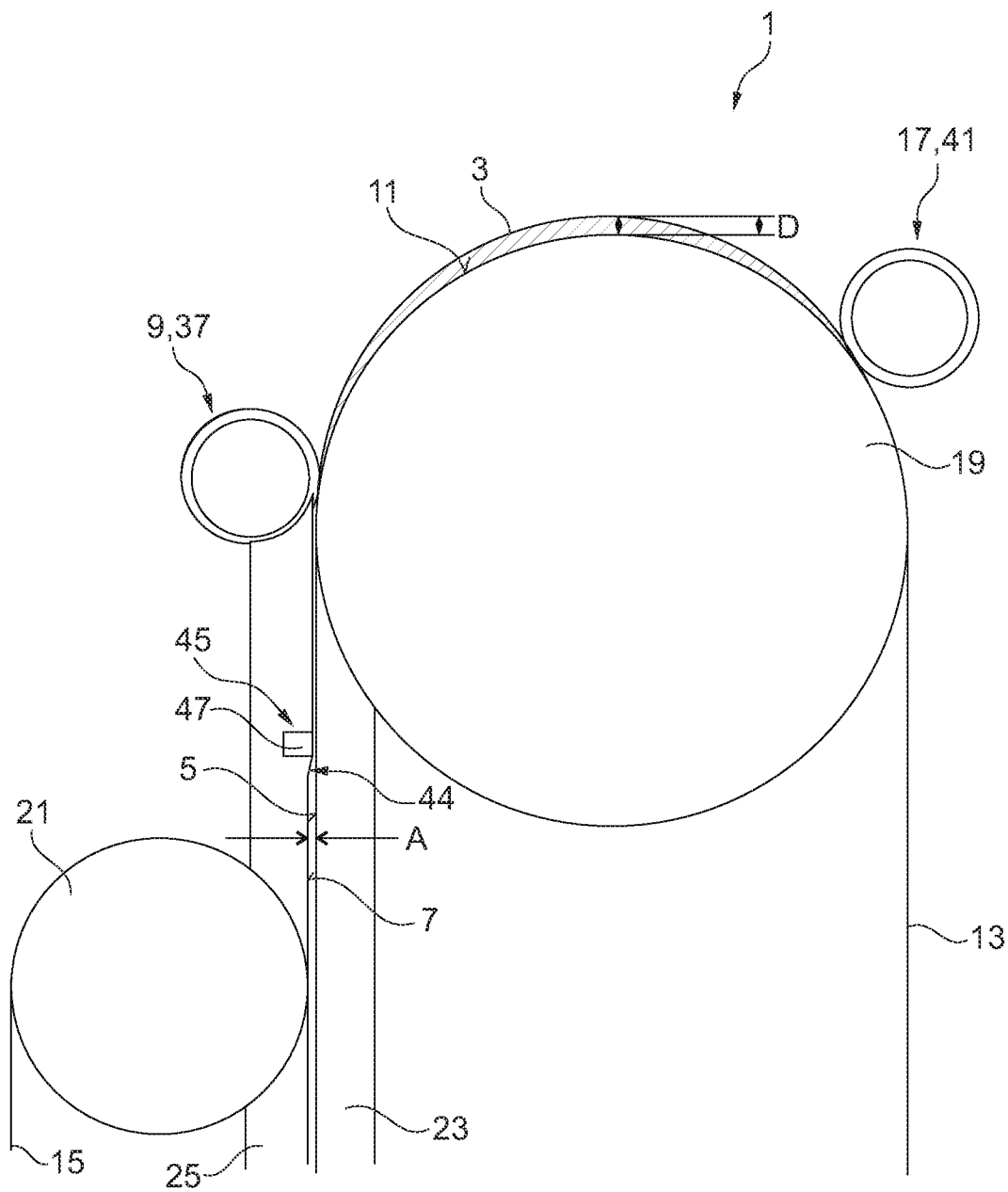
Figure 5:
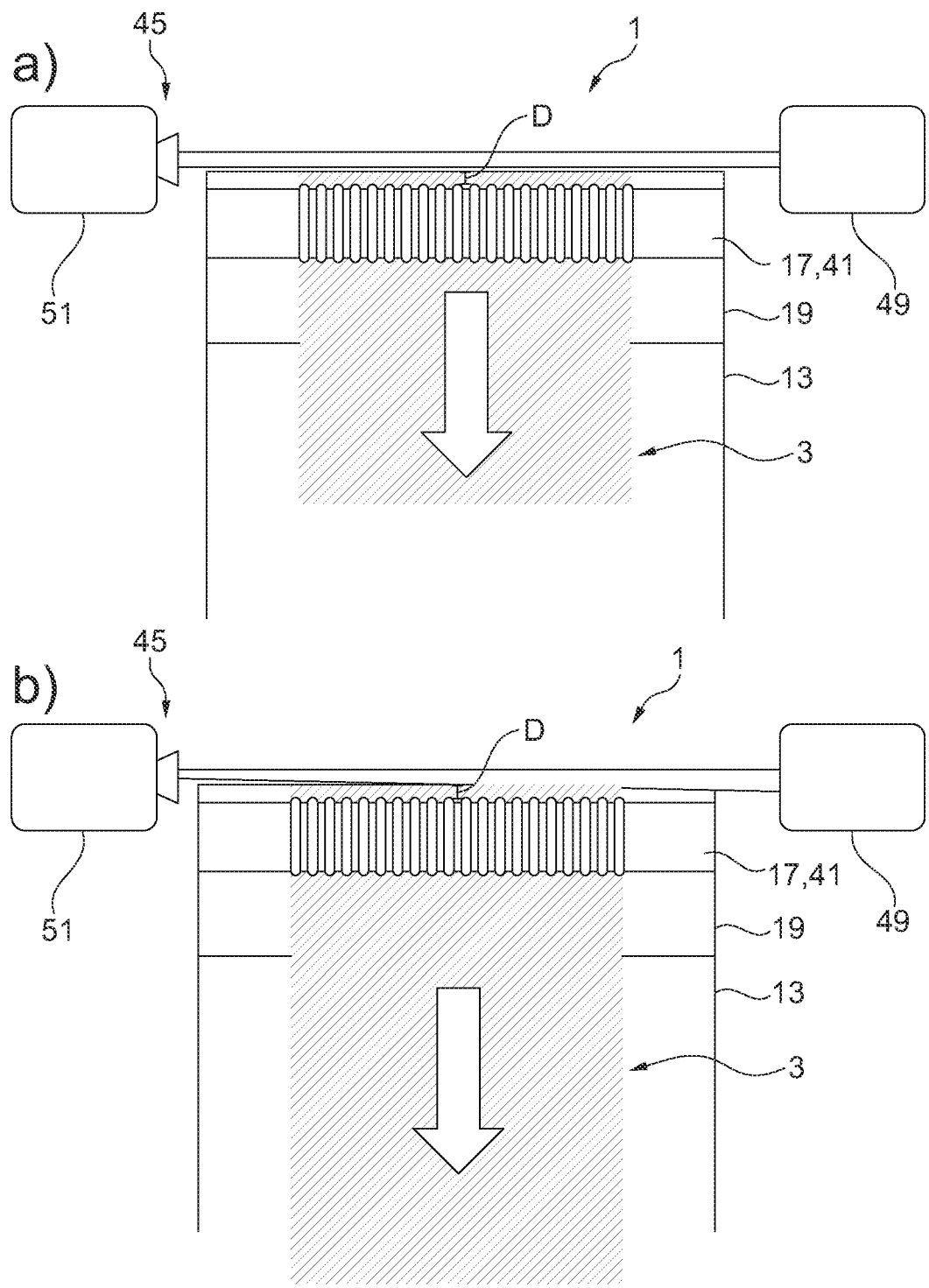
Figure 6:
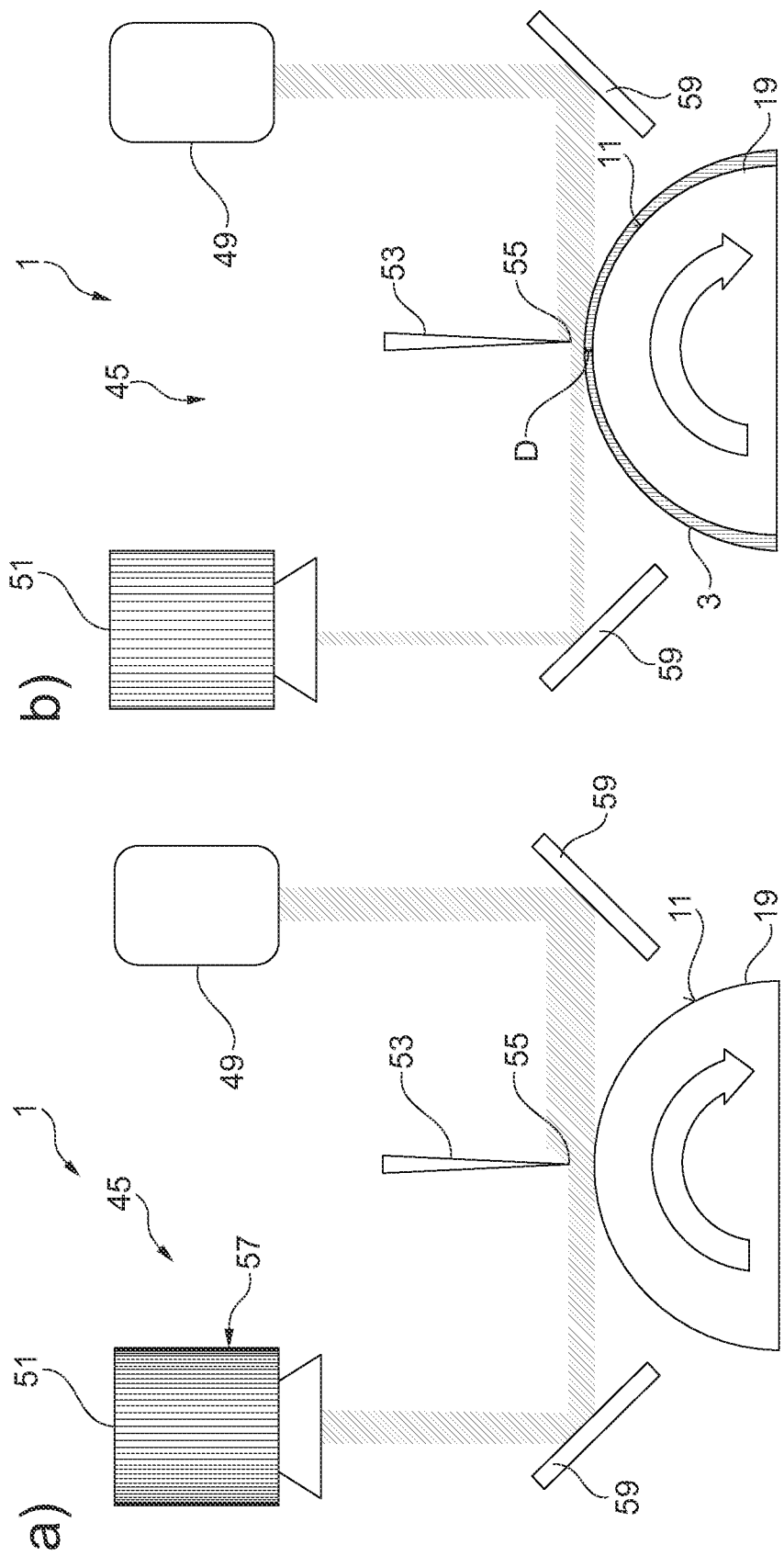

The invention is explained in more detail below with reference to the drawing. Thereby show:

FIG. 1 an illustration of an embodiment of an assembly comprising a first embodiment of a device for generating a liquid film of a liquid medium in a film bag, FIG. 2 a side view of the device according to FIG. 1 in two functional positions, FIG. 3 a top view of the device according to FIG. 1, FIG. 4 a first detailed view of the device according to FIG. 1, FIG. 5 a detailed schematic representation of a second embodiment of the device, and FIG. 6 a detailed schematic representation of a third embodiment of the device.

FIG. 1 shows in particular a schematic representation of a first embodiment of a device 1 for generating a liquid film of a liquid medium in a film bag 3 shown schematically in FIG. 3. The device 1 has two accumulating surfaces spaced apart from one another by an accumulating distance A shown in FIG. 2, namely a first accumulating surface 5 and a second accumulating surface 7, between which the film bag 3 can be arranged and transported along a transport direction, in FIG. 1 vertically upwards. A braking element 9 is arranged downstream of the accumulating surfaces 5, 7 in the transport direction, which is arranged to brake the film bag 3. The device 1 also has a running surface 11 which is convexly curved in the transport direction and is set up and arranged in such a way that the film bag 3 braked by the braking element 9 can be clamped on the running surface 11 behind the braking element 9. In the area of the running surface 11, the transport direction is also deflected according to the curvature of the running surface 11; the transport direction thus follows in particular the curvature of the running surface 11, as does the transported film bag 3.

The first accumulating surface 5 is formed at least in some areas, preferably completely, by a driven first conveyor belt 13, which is arranged to convey the film bag 3 in the transport direction.

In the embodiment shown here, the second accumulating surface 7 is also formed in a preferred manner at least in some areas, preferably completely, by a preferably driven second conveyor belt 15.

The device 1 has a controllable tensioning element 17 downstream of the braking element 9 in the transport direction, which is arranged to span the film bag 3 on the running surface 11 between the braking element 9 and the tensioning element 17. The first conveyor belt 13 or a belt drive for the first conveyor belt 13 can be controlled independently of the controllable tensioning element 17.

With the driven first conveyor belt 13 and the controllable tensioning element 17, it is advantageously possible to adjust, in particular to regulate, the bag tension of the film bag 3 in the area of the running surface 11 on the one hand and the transport speed of the film bag 3 on the other hand independently of each other. In this way in particular, a homogeneous and temporally constant layer thickness of the liquid film in the film bag 3 can be ensured in the region of the running surface 11. This is particularly advantageous with regard to a dose-controlled exposure of the liquid medium to physical radiation to be carried out with the aid of the device 1.

The running surface 11 is preferably formed at least in some areas, preferably completely, by the first conveyor belt 13. In particular, the running surface 11 is arranged here on a first first cylinder roller 19, wherein the first conveyor belt 13 runs on two first cylinder rollers 19, 19', here namely the first first cylinder roller 19 and a second first cylinder roller 19', and is preferably spanned by the first cylinder rollers 19, 19'.

The second conveyor belt 15 preferably runs on two second cylinder rollers 21, 21' and is preferably spanned between the second cylinder rollers 21, 21'. In particular, the first conveyor belt 13 and the second conveyor belt 15 are thus preferably configured as endless belts.

The first conveyor belt 13 is arranged here on a first accumulating plate 23 and is displaceable relative to the first accumulating plate 23. The second conveyor belt 15 is arranged on a second accumulating plate 25 is displaceable relative to the second accumulating plate 25. The film bag 3 can be arranged between the accumulating plates 23, 25 and is transported there by the conveyor belts 13, 15. The accumulating distance A is preferably defined in particular by a distance between the accumulating plates 23, 25.

According to a preferred embodiment, the first conveyor belt 13 and the second conveyor belt 15 are mechanically coupled to each other with respect to their running speed. For this purpose, for example, one of the first cylindrical rollers 19, 19' can advantageously be operatively connected mechanically to one of the second cylindrical rollers 21, 21', for example via a belt drive or gear drive or in another suitable manner, in order to effect a synchronous movement of the conveyor belts 13, 15 by means of a common belt drive.

Alternatively, however, it is possible for the first conveyor belt 13 and the second conveyor belt 15 each to be assigned an independently controllable belt drive, here for example— shown merely schematically—a first belt drive 27 for the first conveyor belt 13 and a second belt drive 29 for the second conveyor belt 15, wherein the running speeds for the first conveyor belt 13 and the second conveyor belt 15 preferably being adjustable—preferably electronically. The belt drives 27, 29 can also be assigned to other cylinder rollers 19, 19', 21, 21' than shown here, in particular in a preferred embodiment to the upper cylinder rollers 19, 21 in the figure.

In particular, the device 1 preferably has a control device 31 that is operatively connected to the at least one belt drive, in particular to the first belt drive 27 and to the second belt drive 29, in a manner not explicitly shown here, in order to control the at least one belt drive, in particular both belt drives 27, 29.

Independently controllable belt drives 27, 29 for the first conveyor belt 13 and the second conveyor belt 15 enable further variation of transport parameters for the film bag 3, wherein it is possible in particular to move the conveyor belts 13, 15 at different speeds or even in different directions.

The device 1 preferably has a temperature control device 33, which is set up to control the temperature of the running surface 11, in particular to heat it. The temperature control device 33 is preferably operatively connected to the control device 31 and can be controlled by the latter.

Alternatively or additionally, the device 1 preferably has a cooling device 35, which is set up to cool the tensioning element 17. In a preferred embodiment, the cooling device 35 is also operatively connected to the control device 31 and can be controlled by the latter.

The device 1 is preferably part of an assembly 2 for controlled exposure of the liquid medium in the film bag 3 to physical radiation. In addition to the device 1, the assembly 2 comprises a radiation source 4 which is arranged to emit physical radiation. The radiation source 4 is arranged in such a way that the film bag 3 can be irradiated by it in the region of the convex running surface 11. In particular, the radiation source 4 is set up to emit particle radiation and/or wave radiation, in particular ionizing radiation, in particular beta radiation, hard or soft X-ray radiation, ultraviolet radiation, visible light, infrared or thermal radiation, tera-hertz radiation, microwave radiation, atomic ion radiation, proton radiation, positron radiation, or another form of physical radiation.

FIG. 2 shows a representation of the device 1 according to FIG. 1 in two different functional positions.

Identical and functionally identical elements are provided with the same reference signs in all figures, so that reference is made to the preceding description in each case.

In FIG. 2, at a), the device 1 is shown in a first functional position, in which the conveyor belts 13, 15 and the accumulating plates 23, 25 are arranged comparatively far apart from one another, so that the accumulating distance A is comparatively large. In this first functional position, the film bag 3 in particular can be inserted between the conveyor belts 13, 15. In b), the conveyor belts 13, 15 and the accumulating plates 23, 25 are arranged closer together in a second functional position, so that the accumulating distance A is smaller. In particular, in this second functional position, the film bag 3 is pressed between the accumulating plates 23, 25 and the conveyor belts 13, 15, as a result of which the liquid medium in the film bag 3 is distributed evenly over a defined volume. By suitably driving the conveyor belts 13, 15, the film bag 3 can now be transported, in particular passed under the radiation source 4.

Overall, at least one of the accumulating surfaces 5, 7, preferably the first accumulating surface 5, is preferably displaceable relative to the other accumulating surface 7, 5 in such a way that the accumulating distance A is adjustable. This can preferably be set to be constant along the transport direction and/or to taper along the transport direction.

FIG. 2 only shows a constant setting of the accumulating distance A. The accumulating surfaces 5, 7 are arranged parallel to each other. If an angle between the accumulating surfaces 5, 7 can also be changed so that the accumulating distance A tapers along the transport direction, in FIG. 2 from vertical down to vertical up, a further degree of freedom is provided for changing the transport conditions for the film bag 3.

FIG. 3 shows a top view of the device 1 according to FIGS. 1 and 2.

The braking element 9 is preferably configured as a brake roller 37. In the embodiment shown here, the brake roller 37 is in a preferred embodiment speed-coupled to the first conveyor belt 13. This is preferably achieved by the brake roller 37 being frictionally connected to the first conveyor belt 13.

Specifically, a plurality of friction rings 39 spaced apart from one another in the axial direction of the brake roller 37 are arranged on the brake roller 37, which are not only in contact with the film bag 3 in a central region of the brake roller 37, but are also in frictional contact with the first conveyor belt 13 in lateral edge regions of the brake roller 37. Thus, in a simple manner, the rotational speed of the brake roller 37 is coupled to the running speed of the first conveyor belt 13. In particular, this represents a special embodiment of a passively braked brake roller 37.

In an alternative embodiment, it is possible that the brake roller 37 is driven independently of the first conveyor belt 13. Alternatively, it can also be actively braked or passively braked in another embodiment, for example by means of a centrifugal brake.

The tensioning element 17 is preferably configured as a tensioning roller 41. Preferably, the tensioning roller 41 is also equipped in certain areas with friction rings 39 arranged at a distance from one another in the axial direction of the tensioning roller 41, but preferably only in a central area where the friction rings 39 only come into frictional contact with the film bag 3; on the other hand, the tensioning roller 41 preferably does not have any friction rings 39 to the side of the area of the film bag 3, so that the tensioning roller 41 is not speed-coupled to the first conveyor belt 13. The control device 31 is preferably operatively connected to the tensioning element 17, in particular to a separate roller drive 43 of the tensioning roller 41, and is set up to control the tensioning element 17, in this case the tensioning roller 41, as a function of a specific, preferably parameterizable layer thickness of the liquid film to be produced, in particular to control the roller drive 43 accordingly. The control is preferably torque-controlled, preferably torque-regulated, or speed-controlled, preferably speed-regulated.

In particular, the frictional contact between the tensioning roller 41 and the film bag 3 preferably spans the cover film of the film bag 3 so that, in cooperation with the brake roller 37, the running surface 11 and the conveyor belts 13, 15, a liquid film of a specific, preferably parameterizable layer thickness can be produced in the film bag 3 on the running surface 11.

The film bag 3 is thus clamped on the upper side of the first conveyor belt 13 between the brake roller 37 and the tensioning roller 41. The brake roller 37 is frictionally coupled to the first conveyor belt 13 and to the film bag 3. The tensioning roller 41 rests on the cover film of the film bag 3 so that the film bag 3 can be clamped between the brake roller 37 and the tensioning roller 41. A defined bag tension results in a homogeneous, temporally constant layer thickness of the liquid medium in the area of the running surface 11. The torque or the speed of the tensioning roller 41 in particular is decisive for setting the layer thickness, in particular depending on whether the bag tension is to be adjusted while maintaining the static friction between the tensioning roller 41 and the cover film, i.e. in particular avoiding a slip between the tensioning roller 41 and the cover film, or whether a temporary slip is permitted, in which case the bag tension is then also adjusted by means of sliding friction between the tensioning roller 41 and the cover film.

FIG. 4 shows a detailed representation of the embodiment example of the device 1 according to FIGS. 1 to 3 in operation, wherein a predetermined layer thickness D of the liquid film in the film bag 3 in the region of the running surface 11, which is to be regulated, is shown here.

In FIG. 4, it can be seen that a distance value of the accumulating distance A is not the same along the entire length of the accumulating surfaces 5, 7. Rather, here the second accumulating surface 7 has a step 44 in an area in front of the braking element 9, at which the accumulating distance A changes, namely from a first, larger distance value in front of the step 44 to a second, smaller distance value behind the step 44.

In order to be able to control the bag tension, in particular by suitable control of the tensioning element 17, a measuring device 45 is preferably provided which is set up to determine the layer thickness D, either directly or indirectly, it being sufficient for the measuring device 45 to provide a measured variable which can be controlled to set a homogeneous and temporally constant layer thickness D, without the layer thickness D itself having to be explicitly determined for this purpose.

The measuring device 45 is preferably set up to determine the layer thickness D by means of pressure measurement, optically, electrically or electronically, and/or by detecting a flow velocity of the liquid medium in the film bag 3.

The measuring device 45 is preferably operatively connected to the control device 31, so that the measured variable detected by the measuring device 45 is available in the control device 31.

In the example shown in FIG. 4, the measuring device 45 is configured as a pressure sensor 47. By means of the pressure sensor 47, in particular, a pressure can be detected as a measure of a flow resistance for the liquid medium, wherein preferably the detected pressure can be adjusted to a constant value for setting a constant layer thickness D.

FIG. 5 shows a schematic representation of a second embodiment of the device 1. Here, the measuring device 45 is configured as an optical measuring device that directly detects the layer thickness D by detecting the shading of a light source 49 on a sensor 51. The light source 49 can in particular be an LED or laser diode. The sensor 51 can in particular be a phototransistor, a photodiode, a line sensor, or a camera, in particular a line camera or matrix camera. In this case, the sensor 51 is mounted in the region of the running surface 11 in particular opposite the light source 49 transversely to the transport direction, in particular perpendicularly to the transport direction, in particular in such a way that a light line generated by the light source 49 extends along the maximum of the running surface 11 and thus precisely in the region in which the layer thickness D is to be measured.

If the layer thickness D increases, a sensor surface of the sensor 51 is increasingly shadowed. Conversely, if the layer thickness D decreases, more light is transmitted from the light source 49 to the sensor 51. In this way, the highest point of the liquid film in particular can be detected. For in-line quality control, the maximum value of the film thickness D is decisive, since at this point the depth dose distribution exhibits its greatest inhomogeneity during irradiation. The value measured in this way can be fed to a control algorithm which then controls the tensioning roller 41 in particular in order to adjust the bag tension of the film bag 3 accordingly.

In a), the film bag 3 in FIG. 5 is shown with a smaller layer thickness D; in b), the film bag 3 has, in particular, an inhomogeneous and, in any case, greater layer thickness D in certain areas.

FIG. 6 shows a schematic representation of a third embodiment of the device 1. Here, the measuring device 45 is set up for optical interference measurement, with a light source 49, which is set up to emit coherent light radiation, and a sensor 51, which is set up to detect an interference pattern. The light source 49 can be configured in particular as a laser, in particular a laser diode. The sensor 51 is preferably a camera or a line sensor.

In the region of the maximum of the running surface 11 and thus the region in which the layer thickness D is to be measured, the measuring device 45 has a gap-forming element 53, in this case a wedge, which extends along the running surface 11 transversely with respect to the transport direction, in particular perpendicularly with respect to the transport direction, a gap-forming end 55, in particular a pointed end of the gap-forming element 53 facing the running surface 11 and being arranged at a distance from the running surface 11 in such a way that a gap is formed with a size at which interference of the radiation emitted by the light source 49 can be detected in the sensor 51, even if no film bag 3 is arranged in the device 1.

The width of the gap formed in this way is then defined by the fixed assembly of the gap-forming element 53 on the one hand and the layer thickness D of the liquid film in the film bag 3 on the other.

An interference pattern 57 detectable in the sensor 51 is dependent on the instantaneous width of the gap and thus directly dependent on the layer thickness D. Here, a) shows a situation in which no film bag 3 is arranged in the device 1. Here, the interference pattern 57 has a smaller spatial period.

At b) a situation is shown in which a film bag 3 with a finite layer thickness D of the liquid medium is arranged on the running surface 11. As a result, the gap is narrowed and the interference pattern 57 has a larger spatial period. Based on the spatial period of the interference pattern 57, the layer thickness D can be directly inferred.

The light from the light source 49 is deflected twice here by two deflection mirrors 59. However, this is not absolutely necessary.

A measurement of the layer thickness D can also be otherwise acquired by imaging techniques directly or indirectly, as well as by methods for determining the flow velocity of the liquid medium within the film bag 3.

As part of a process for generating a liquid film of a liquid medium in a film bag 3, the film bag 3 is transported through the device 1 in the transport direction. A uniform liquid film, preferably with a constant layer thickness over time, is produced by independently controlling at least the belt drive 27 for the first conveyor belt 13, or a common belt drive for both conveyor belts 13, 15, on the one hand, and the tensioning element 17 on the other.

The invention claimed is:

1. A method for generating a liquid film of a liquid medium in a film bag, the method comprising:
    providing a device including:
    two accumulating surfaces spaced apart by an accumulating distance, between which the film bag is arrangeable for transportation along a transport direction;
    a braking element arranged downstream of the accumulating surfaces in the transport direction, which braking element is arranged to brake the film bag;
    a running surface convexly curved in the transport direction and set up and arranged such that the film bag braked by the braking element is spanned on the running surface behind the braking element, wherein at least a first accumulating surface of the two accumulating surfaces is formed at least in regions by a driven first conveyor belt which is arranged to convey the film bag in the transport direction;
    a controllable tensioning element downstream of the braking element in the transport direction, the controllable tensioning element arranged to span the film bag on the running surface between the braking element and the tensioning element; and
    a control device operatively connected to the tensioning element and to one of the first conveyor belt and a belt drive for the first conveyor belt to control a running speed of the first conveyor belt, the one of the first conveyor belt and the belt drive for the first conveyor belt being controllable independently of the controllable tensioning element; and
    transporting the film bag in the transport direction through the device and
    producing a uniform liquid film having a temporally constant layer thickness by controlling at least one belt drive for the first conveyor belt and the tensioning element independently of one another.

2. The method according to claim 1, wherein a second accumulating surface of the two accumulating surfaces is formed at least in regions by a driven second conveyor belt.

3. The method according to claim 2, wherein the first conveyor belt is arranged on a first accumulating plate so as to be displaceable relative to the first accumulating plate, wherein the second conveyor belt is arranged on a second accumulating plate so as to be displaceable relative to the second accumulating plate, wherein the film bag is arranged between the accumulating plates for transportation by the conveyor belts.

4. The method according to claim 2, wherein
   a) the first conveyor belt and the second conveyor belt are mechanically coupled to each other with respect to their running speed, or
   b) the first conveyor belt and the second conveyor belt are each assigned an independently controllable belt drive.

5. The method according to claim 4, wherein running speeds for the first conveyor belt and the second conveyor belt are adjustable.

6. The method according to claim 1, wherein at least one of the accumulating surfaces is displaceable relative to the other accumulating surface in such a way that the accumulating distance is adjustable, wherein the accumulating distance is adjustable
    constant along the transport direction, and/or
    tapering along the transport direction.

7. The method according to claim 1, wherein the braking element is configured as a brake roller which is
    speed-coupled with the first conveyor belt,
    driven independently of the first conveyor belt, or
    actively or passively braked.

8. The method according to claim 1, wherein the tensioning element is configured as a tensioning roller, wherein the control device controls the tensioning element as a function of a specific, parameterizable layer thickness of the liquid film to be produced
    torque-controlled, or
    speed-controlled.

9. The method according to claim 1, with
    a temperature control device arranged to temper the running surface, and/or with
    a cooling device arranged to cool the tensioning element.

10. The method according to claim 1, further comprising a measuring device for determining a layer thickness of the liquid film to be produced, wherein the measuring device is set up to determine the layer thickness by pressure measurement, optically, electrically or electronically, and/or by detecting a flow rate of the liquid medium in the film bag.

11. The method of claim 1, wherein the device is part of an assembly for controlled exposure of the liquid medium in the film bag to physical radiation, and the assembly including a radiation source of physical radiation, the method further comprising irradiating the film bag in a region of the running surface.

* * * * *